United States Patent
Raikar et al.

(10) Patent No.: US 9,657,022 B2
(45) Date of Patent: May 23, 2017

(54) 7-OXO-1,6-DIAZABICYCLO[3.2.1]OCTANE DERIVATIVES AND THEIR USE AS ANTIBACTERIAL AGENTS

(71) Applicant: WOCKHARDT LIMITED, Aurangabad (IN)

(72) Inventors: Sanjay Raikar, Aurangabad (IN); Sanjay Kisan Dabhade, Maharashtra (IN); Laxmikant Pavase, Maharashtra (IN); Sachin Bhagwat, Aurangabad (IN); Ravindra Dattatraya Yeole, Maharashtra (IN); Mahesh Vithalbhai Patel, Maharashtra (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/106,305

(22) PCT Filed: Jan. 21, 2015

(86) PCT No.: PCT/IB2015/050462
§ 371 (c)(1),
(2) Date: Jun. 19, 2016

(87) PCT Pub. No.: WO2015/110966
PCT Pub. Date: Jul. 30, 2015

(65) Prior Publication Data
US 2017/0044159 A1    Feb. 16, 2017

(30) Foreign Application Priority Data
Jan. 21, 2014  (IN) .................. 192/MUM/2014

(51) Int. Cl.
| | | |
|---|---|---|
| A61K 31/439 | (2006.01) |
| C07D 471/08 | (2006.01) |
| A61K 31/445 | (2006.01) |
| A61K 31/496 | (2006.01) |
| A61K 31/546 | (2006.01) |
| A61K 31/695 | (2006.01) |
| A61K 45/06 | (2006.01) |
| C07F 7/18 | (2006.01) |
| A61K 31/407 | (2006.01) |
| A61K 31/424 | (2006.01) |

(52) U.S. Cl.
CPC .......... *C07D 471/08* (2013.01); *A61K 31/407* (2013.01); *A61K 31/424* (2013.01); *A61K 31/439* (2013.01); *A61K 31/445* (2013.01); *A61K 31/496* (2013.01); *A61K 31/546* (2013.01); *A61K 31/695* (2013.01); *A61K 45/06* (2013.01); *C07F 7/1856* (2013.01)

(58) Field of Classification Search
CPC ............................ A61K 31/439; C07D 471/08
USPC .......................................... 514/300; 546/121
See application file for complete search history.

(56) References Cited

U.S. PATENT DOCUMENTS

| | | | |
|---|---|---|---|
| 8,796,257 B2 * | 8/2014 | Maiti ................ | C07D 519/00 514/210.21 |
| 8,822,450 B2 * | 9/2014 | Patel ................ | A61K 31/4545 514/119 |
| 2013/0225554 A1 | 8/2013 | Maiti et al. | |

FOREIGN PATENT DOCUMENTS

WO    WO2013030733 A1    3/2013

* cited by examiner

*Primary Examiner* — Charanjit Aulakh
(74) *Attorney, Agent, or Firm* — Bio Intellectual Property Services LLC (Bio IPS); O. (Sam) Zaghmout

(57) ABSTRACT

Compounds of Formula (I), their preparation, and use in preventing or treating a bacterial infection are disclosed.

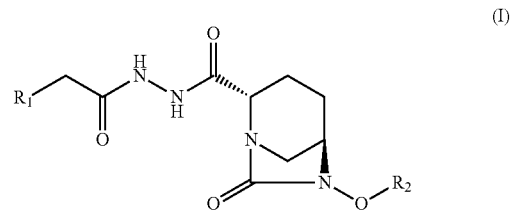

(I)

18 Claims, No Drawings

7-OXO-1,6-DIAZABICYCLO[3.2.1]OCTANE DERIVATIVES AND THEIR USE AS ANTIBACTERIAL AGENTS

RELATED PATENT APPLICATIONS

This application claims priority to Indian Patent Application No. 192/MUM/2014 filed on Jan. 21, 2014, the disclosures of which are incorporated herein by reference in its entirety as if fully rewritten herein.

FIELD OF THE INVENTION

The invention relates to nitrogen containing compounds, their preparation and their use in preventing or treating infections.

BACKGROUND OF INVENTION

Emergence of bacterial resistance to known antibacterial agents is becoming a major challenge in treating bacterial infections. One way forward to treat bacterial infections, and especially those caused by resistant bacteria, is to develop newer antibacterial agents that can overcome the bacterial resistant. Coates et al. (*Br. J. Pharmacol.* 2007; 152(8), 1147-1154.) have reviewed novel approaches to developing new antibiotics. However, the development of new antibacterial agents is a challenging task. For example, Gwynn et al. (*Annals of the New York Academy of Sciences,* 2010, 1213: 5-19) have reviewed the challenges in discovery of antibacterial agents.

Several compounds have been described in the prior art for the use in treatment of bacterial infections (for example, see Patent Application Nos. PCT/IB2012/054296, PCT/IB2012/054290, US20130225554, PCT/US2010/060923, PCT/EP2010/067647, PCT/US2010/052109, PCT/US2010/048109, PCT/GB 2009/050609, PCT/EP2009/056178, PCT/US2009/041200, PCT/IB2013/053092 and PCT/IB2012054706). However, there remains a need for potent antibacterial agents for preventing and/or treating bacterial infections, including those caused by bacteria that are resistant to known antibacterial agents.

The inventors have now surprisingly discovered novel nitrogen containing compounds having potent antibacterial activity.

SUMMARY OF THE INVENTION

Accordingly, there are provided nitrogen containing compounds, methods for preparation of these compounds, pharmaceutical compositions comprising these compounds, and method for preventing or treating a bacterial infection in a subject using these compounds.

In one general aspect, there are provided compounds of Formula (I):

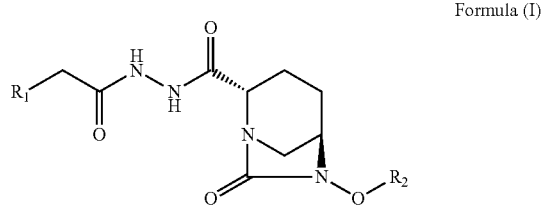

Formula (I)

or a stereoisomer or a pharmaceutically acceptable derivative thereof;
wherein:
$R_1$ is:
(a) cycloalkyl optionally substituted with one or more substituents independently selected from $C_1$-$C_6$ alkyl, halogen, CN, $OR_3$, $NR_3R_4$, or $CONR_3R_4$, or
(b) heterocycloalkyl optionally substituted with one or more substituents independently selected from $C_1$-$C_6$ alkyl, halogen, CN, $OR_3$, $NR_3R_4$, or $CONR_3R_4$;
$R_2$ is:
(a) $SO_3M$,
(b) $CF_2COOM$,
(c) CHFCOOM,
(d) $CH_2COOM$, or
(e) $CF_3$;
$R_3$ and $R_4$ are each independently:
(a) hydrogen, or
(b) $C_1$-$C_6$ alkyl optionally substituted with one or more substitutents independently selected from halogen, CN, OH, $O(C_1$-$C_6$ alkyl), $NH(C_1$-$C_6$ alkyl), $N(C_1$-$C_6$ alkyl)$_2$, $CONH(C_1$-$C_6$ alkyl), $CON(C_1$-$C_6$ alkyl)$_2$, cyclo alkyl, hetero cyclo alkyl, aryl or heteroaryl;
M is hydrogen or a cation.

In another general aspect, there are provided pharmaceutical compositions comprising a compound of Formula (I) or a stereoisomer or a pharmaceutically acceptable derivative thereof.

In another general aspect, there are provided methods for preventing or treating a bacterial infection in a subject, said methods comprising administering to said subject a compound of Formula (I) or a stereoisomer or a pharmaceutically acceptable derivative thereof.

In yet another general aspect, there are provided methods for preventing or treating a bacterial infection in a subject, said methods comprising administering to said subject a pharmaceutical composition comprising a compound of Formula (I) or a stereoisomer or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof.

In another general aspect, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In another general aspect, there are provided pharmaceutical compositions comprising: (a) a compound of Formula (I) or a stereoisomer or a pharmaceutically acceptable derivative thereof, (b) at least one beta-lactamase inhibitor or a pharmaceutically acceptable derivative thereof, and (c) at least one antibacterial agent or a pharmaceutically acceptable derivative thereof.

In another general aspect, there are provided methods for preventing or treating a bacterial infection in a subject, said methods comprising administering to said a pharmaceutical composition comprising: (a) a compound of Formula (I) or a stereoisomer or a pharmaceutically acceptable derivative thereof, and (b) at least one beta-lactamase inhibitor or a pharmaceutically acceptable derivative thereof.

In another general aspect, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent or pharmaceutically acceptable derivative thereof.

In another aspect, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or a pharmaceutically acceptable derivative thereof.

In another general aspect, there are provided methods for preventing or treating a bacterial infection in a subject, said methods comprising administering to said subject: (a) a compound of Formula (I) or a stereoisomer or a pharmaceutically acceptable derivative thereof, and (b) at least one beta-lactamase inhibitor or pharmaceutically acceptable derivative thereof.

In another general aspect, there are provided methods for preventing or treating a bacterial infection in a subject, said methods comprising administering to said subject: (a) a compound of Formula (I) or a stereoisomer or a pharmaceutically acceptable derivative thereof, and (b) at least one antibacterial agent or pharmaceutically acceptable derivative thereof.

In another general aspect, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In another general aspect, there are provided methods for increasing antibacterial effectiveness of an antibacterial agent in a subject, said method comprising co-administering said antibacterial agent or a pharmaceutically acceptable derivative thereof, with a compound of Formula (I) or a stereoisomer or a pharmaceutically acceptable derivative thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, which would occur to one skilled in the relevant art and having possession of this disclosure, are to be considered within the scope of the invention. It must be noted that, as used in this specification and the appended claims, the singular forms "a", "an", and "the" include plural referents unless the content clearly dictates otherwise. All references including patents, patent applications, and literature cited in the specification are expressly incorporated herein by reference in their entirety.

The inventors have surprisingly discovered novel nitrogen containing compounds having antibacterial properties.

The term "$C_1$-$C_6$ alkyl" as used herein refers to branched or unbranched acyclic hydrocarbon radical with 1 to 6 carbon atoms. Typical non-limiting examples of "$C_1$-$C_6$ alkyl" include methyl, ethyl, n-propyl, iso-propyl, n-butyl, sec-butyl, iso-butyl, tert-butyl, n-pentyl, iso-pentyl, tert-pentyl, neopentyl, sec-pentyl, 3-pentyl, n-hexyl, 2-methylpentyl, 3-methylpentyl, 2,2-dimethylbutyl, 2,3-dimethylbutyl and the like. The "$C_1$-$C_6$ alkyl" may be unsubstituted, or substituted with one or more substituents. Typical, non-limiting examples of such substituents include halogen, alkoxy, CN, SH, COOH, COOC$_1$-C$_6$alkyl, CONH$_2$, OH, NH$_2$, NHCOCH$_3$, cycloalkyl, heterocycloalkyl, heteroaryl, aryl and the like.

The term "cycloalkyl" as used herein refers to three to seven member cyclic hydrocarbon radicals. The cycloalkyl group optionally incorporates one or more double or triple bonds, or a combination of double or triple bonds, but which is not aromatic. Typical, non-limiting examples of cycloalkyl groups include cyclopropyl, cyclobutyl, cyclopentyl, cyclohexyl, and cycloheptyl. The cycloalkyl may be unsubstituted, or substituted with one or more substituents. Typical, non-limiting examples of such substituents include $C_1$-$C_6$ alkyl, halogen, alkoxy, CN, SH, COOH, COOC$_1$-C$_6$alkyl, CONH$_2$, OH, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like.

The term "heterocycloalkyl" as used herein refers to four to seven member cycloalkyl group containing one or more heteroatoms selected from nitrogen, oxygen or sulfur. The heterocycloalkyl group optionally incorporates one or more double or triple bonds, or a combination of double bonds and triple bonds, but which is not aromatic. Typical, non-limiting example of heterocycloalkyl groups include azetidinyl, pyrrolidinyl, 2-oxo-pyrrolidinyl, imidazolidin-2-one-yl, piperidinyl, oxazinyl, thiazinyl, piperazinyl, piperazin-2,3-dione-yl, morpholinyl, thiomorpholinyl, azepanyl, and the like. The heterocycloalkyl may be unsubstituted, or substituted with one or more substituents. Typical, non-limiting examples of such substituents include $C_1$-$C_6$ alkyl, halogen, alkoxy, CN, COOH, CONH$_2$, OH, NH$_2$, NHCOCH$_3$, heteroaryl, aryl, SO$_2$-alkyl, SO$_2$-aryl, OSO$_2$-aryl and the like.

The term "aryl" as used herein refers to a monocyclic or polycyclic aromatic hydrocarbon. Typical, non-limiting examples of aryl groups include phenyl, naphthyl, anthracenyl, fluorenyl, phenanthrenyl, indenyl and the like. The aryl group may be unsubstituted, or substituted with one or more substituents. Typical, non-limiting examples of such substituents include C1-C6 alkyl, halogen, alkoxy, CN, COOH, CONH$_2$, OH, NH$_2$, NHCOCH$_3$, heterocycloalkyl, heteroaryl, aryl, SO$_2$-alkyl, SO$_2$-aryl, OSO$_2$-alkyl, OSO$_2$-aryl and the like. In some embodiments, the term "aryl" refers to a monocyclic or polycyclic aromatic hydrocarbon radical containing up to 14 ring atoms.

The term "heteroaryl" as used herein refers to a monocyclic or polycyclic aromatic hydrocarbon group wherein one or more carbon atoms have been replaced with heteroatoms selected from nitrogen, oxygen, and sulfur. If the heteroaryl group contains more than one heteroatom, the heteroatoms may be the same or different. Typical, non-limiting example of heteroaryl groups include pyridyl, pyrimidinyl, pyrazinyl, pyridazinyl, triazinyl, furanyl, pyrrolyl, thienyl, oxadiazolyl, thiadiazolyl, tetrazolyl, oxazolyl, thiazolyl, imidazolyl, pyrazolyl, triazonyl, isoxazolyl, oxadiazolyl, oxatriazolyl, isothiazolyl, thiatriazolyl, thiazinyl, oxazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-pyridazinyl, purinyl, benzofuranyl, isobenzofuranyl, benzothienyl, benzothiophenyl, carbazolyl, benzimidazolyl, benzoxazolyl, benzoisoxazolyl, benzothiazolyl, benzotriazolyl, indolyl, isoindolyl, quinolinyl, isoquinolinyl, acridinyl, naphthothienyl, thianthrenyl, chromenyl, xanthenyl, phenoxathienyl, indolizinyl, indazolyl, phthalazinyl, naphthyridinyl, qinoxalinyl, quinazolinyl, cinnolinyl, pteridinyl, beta-carbolinyl, phenanthridinyl, phenanthrolinyl, phenazinyl, phenothiazinyl, phenoxazinyl and the like. The heteroaryl group may be unsubstituted, or substituted with one or more substituents. Typical, non-limiting examples of such substituents include C1-C6 alkyl, halogen, alkoxy, CN, COOH, $CONH_2$, OH, SH, $SCH_3$, $NH_2$, $NHCOCH_3$, heterocycloalkyl, heteroaryl, aryl, $SO_2$-alkyl, $SO_2$-aryl, $OSO_2$-alkyl, $OSO_2$-aryl and the like. In some embodiments, the term "heteroaryl" refers to a monocyclic or polycyclic aromatic hydrocarbon radical containing up to 14 ring atoms.

The term "stereoisomers" as used herein refers to compounds that have identical chemical constitution, but differ with regard to the arrangement of their atoms or groups in space. The compounds of Formula (I) may contain asymmetric or chiral centers and, therefore, exist in different stereoisomeric forms. It is intended, unless specified otherwise, that all stereoisomeric forms of the compounds of Formula (I) as well as mixtures thereof, including racemic mixtures, form part of the present invention. In addition, the present invention embraces all geometric and positional isomers (including cis and trans-forms), as well as mixtures thereof, are embraced within the scope of the invention. In general, a reference to a compound is intended to cover its stereoisomers and mixture of various stereoisomers.

The term "optionally substituted" as used herein means that the substitution is optional and therefore includes both unsubstituted and substituted atoms and moieties. A "substituted" atom or moiety indicates that any hydrogen on the designated atom or moiety can be replaced with a selection from the indicated substituent group, provided that the normal valency of the designated atom or moiety is not exceeded, and that the substitution results in a stable compound.

The term "pharmaceutically acceptable derivative" as used herein refers to and includes any pharmaceutically acceptable salt, pro-drugs, metabolites, esters, ethers, hydrates, polymorphs, solvates, complexes or adducts of a compound described herein which, upon administration to a subject, is capable of providing (directly or indirectly) the parent compound. For example, the term "antibacterial or a pharmaceutically acceptable derivative thereof" includes all derivatives of the antibacterial agent (such as salt, prodrugs, metabolites, esters, ethers, hydrates, polymorphs, solvates, complexes or adducts) which, upon administration to a subject, is capable of providing (directly or indirectly) the antibacterial compound.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to salts that are suitable for use in contact with the tissues of human and animals without undue toxicity, irrigation, allergic response and the like, and are commensurate with a reasonable benefit/risk ratio. Pharmaceutically acceptable salts are well known in the art. For example, S. M. Berge, et al. (*J. Pharmaceutical Sciences*, 66; 1-19, 1977), incorporated herein by reference in its entirety, describes various pharmaceutical acceptable salts in details.

In general, the compounds according to the invention contain basic (e.g. nitrogen atoms) as well as acid moieties (e.g. compounds of Formula (I) wherein M is hydrogen). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional group capable of being converted into salt, each such functional group may be converted to salt independently. For example, in case of compounds containing two basic nitrogen atoms, one of the basic nitrogen can form salt with one acid while the other basic nitrogen can form salt with another acid. Some compounds according to the invention contain both acidic as well as basic moieties, and thus can form inner salts or corresponding zwitterions. In general, all pharmaceutically acceptable salt forms of compound of Formula (I) according to invention including acid addition salts, base addition salts, zwitterions or the like are contemplated to be within the scope of the present invention and are generically referred to as pharmaceutically acceptable salts.

The term "halogen" or "halo" as used herein includes chlorine, bromine, fluorine or iodine.

The term "OBn" as used herein refers to benzyloxy.

The term "EDC" as used herein refers to 1-ethyl-3-(3-dimethylamino propyl)carbodiimide.

The term "HOBt" as used herein refers to 1-hydroxybenzotriazole.

The term "Boc" as used herein refers to tert-butyloxycarbonyl

The term "infection" or "bacterial infection" as used herein includes presence of bacteria, in or on a subject, which, if its growth were inhibited, would result in a benefit to the subject. As such, the term "infection" in addition to referring to the presence of bacteria also refers to normal floras, which are not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the type/nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop or mouthwash. In case of a pharmaceutical composition comprising more than one ingredient (active or inert), one of the way of administering such composition is by admixing the ingredients (e.g. in the form of a suitable unit dosage form such as tablet, capsule, solution, powder or like) and then administering the dosage form. Alternatively, the ingredients may also be administered separately (simultaneously or one after the other) as long as these ingredients reach beneficial therapeutic levels such that the composition as a whole provides a synergistic and/or desired effect.

The term "growth" as used herein refers to a growth of one or more microorganisms and includes reproduction or population expansion of the microorganism (e.g. bacteria). The term also includes maintenance of on-going metabolic processes of a microorganism, including the processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to prevent or treat the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyze the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "Extended spectrum beta-lactamase or ESBL" as used herein includes those beta-lactamase enzymes which are capable of conferring bacterial resistance to the penicillins, first-, second-, and third-generation cephalosporins, and aztreonam by hydrolysis of these antibiotics.

The term "pharmaceutically inert ingredient" or "carrier" or "excipient" refers to a compound or material used to facilitate administration of a compound, for example, to increase the solubility of the compound. Solid carriers include, e.g., starch, lactose, dicalcium phosphate, sucrose, and kaolin. Liquid carriers include, e.g., sterile water, saline, buffers, non-ionic surfactants, and edible oils such as oil peanut and sesame oils. In addition, various adjuvants commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8$^{th}$ Ed., Pergamon Press., which is incorporated herein by reference in its entirety.

The term "subject" as used herein refers to vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

In general, the term "cation" includes H, Na, K, Mg, Ca, $NH_4^+$, $(CH_3CH_2)_3N^+$ etc.

In one general aspect, there are provided compounds of Formula (I):

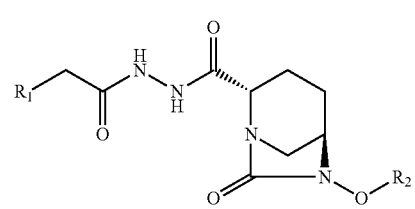

Formula (I)

or a stereoisomer or a pharmaceutically acceptable derivative thereof;

wherein:
R$_1$ is:
(a) cycloalkyl optionally substituted with one or more substituents independently selected from C$_1$-C$_6$ alkyl, halogen, CN, OR$_3$, NR$_3$R$_4$, or CONR$_3$R$_4$, or
(b) heterocycloalkyl optionally substituted with one or more substituents independently selected from C$_1$-C$_6$ alkyl, halogen, CN, OR$_3$, NR$_3$R$_4$, or CONR$_3$R$_4$;

R$_2$ is:
(a) SO$_3$M,
(b) CF$_2$COOM,
(c) CHFCOOM,
(d) CH$_2$COOM, or
(e) CF$_3$;

R$_3$ and R$_4$ are each independently:
(a) hydrogen, or
(b) C$_1$-C$_6$ alkyl optionally substituted with one or more substitutents independently selected from halogen, CN, OH, O(C$_1$-C$_6$ alkyl), NH(C$_1$-C$_6$ alkyl), N(C$_1$-C$_6$ alkyl)$_2$, CONH(C$_1$-C$_6$ alkyl), CON(C$_1$-C$_6$ alkyl)$_2$, cycloalkyl, heterocycloalkyl, aryl or heteroaryl;

M is hydrogen or a cation.

Typical, non-limiting examples of compounds according to the invention include:
(2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester;
(2S,5R)-sulfuric acid mono-{2-[N'-(2-azetidin-3-yl-acetyl)-hydrazinocarbonyl]-7-oxo-1,6-diaza-bicyclo[3.2.1]oct-6-yl}ester;
(2S,5R)-sulfuric acid mono-{2-[N'-(2-(S)-piperidin-2-yl-acetyl)-hydrazinocarbonyl]-7-oxo-1,6-diaza-bicyclo[3.2.1]oct-6-yl}ester;
(2S,5R)-sulfuric acid mono-{2-[N'-(2-(R)-piperidin-2-yl-acetyl)-hydrazinocarbonyl]-7-oxo-1,6-diaza-bicyclo[3.2.1]oct-6-yl}ester;
(2S,5R)-sulfuric acid mono-{2-[N'-(2-(S)-piperidin-3-yl-acetyl)-hydrazinocarbonyl]-7-oxo-1,6-diaza-bicyclo[3.2.1]oct-6-yl}ester;
(2S,5R)-sulfuric acid mono-{2-[N'-(2-piperidin-4-yl-acetyl)-hydrazinocarbonyl]-7-oxo-1,6-diaza-bicyclo[3.2.1]oct-6-yl}ester;
(2S,5R)-sulfuric acid mono-{2-[N'-(2-(RS)-piperazin-2-yl-acetyl)-hydrazinocarbonyl]-7-oxo-1,6-diaza-bicyclo[3.2.1]oct-6-yl}ester;
or a stereoisomer, or a pharmaceutically acceptable derivative thereof.

In general, the compounds of the invention can be prepared according to the general procedures given in Schemes 1 and 2. A person of skills in the art would appreciate that the described method can be varied or optimized further to provide the desired and related compounds. In the following procedures, all variables are as defined above.

In some embodiments, there is provided a process for preparation of compounds of Formula (I):

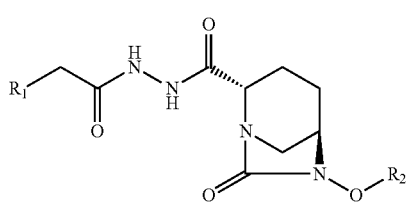

Formula (I)

or a stereoisomer or a pharmaceutically acceptable derivative thereof;
wherein
R$_1$ is:
(a) cycloalkyl optionally substituted with one or more substituents independently selected from C$_1$-C$_6$ alkyl, halogen, CN, OR$_3$, NR$_3$R$_4$, or CONR$_3$R$_4$, or
(b) heterocycloalkyl optionally substituted with one or more substituents independently selected from C$_1$-C$_6$ alkyl, halogen, CN, OR$_3$, NR$_3$R$_4$, or CONR$_3$R$_4$;

R$_2$ is SO$_3$M;
R$_3$ and R$_4$ are each independently:
(c) hydrogen, or
(d) C$_1$-C$_6$ alkyl optionally substituted with one or more substitutents independently selected from halogen, CN, OH, O(C$_1$-C$_6$ alkyl), NH(C$_1$-C$_6$ alkyl), N(C$_1$-C$_6$ alkyl)$_2$, CONH(C$_1$-C$_6$ alkyl), CON(C$_1$-C$_6$ alkyl)$_2$, cyclo alkyl, hetero cyclo alkyl, aryl or heteroaryl;

M is hydrogen or a cation;
said process comprising:
(a) reacting a compound of Formula (Ia) with R$_1$CONHNH$_2$(Ib) in presence of coupling agent to obtain a compound of Formula (Ic);

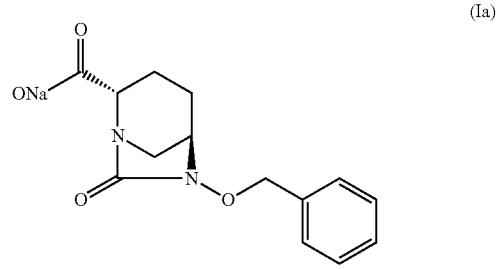

(Ia)

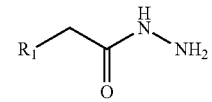

(Ib)

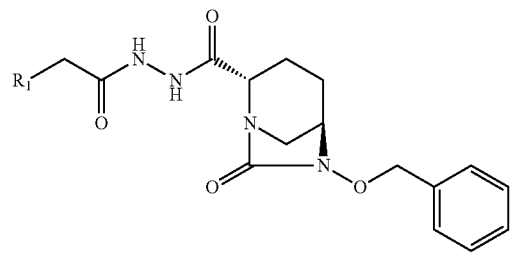

(Ic)

(b) hydrogenolysis of a compound of Formula (Ic) to obtain a compound of Formula (Id);

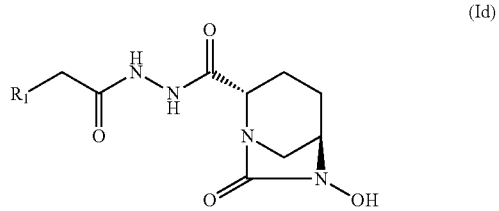

(Id)

(c) sulfonating a compound of Formula (Id), followed by the treatment with tetrabutyl ammonium hydrogen sulfate to obtain a compound of Formula (Ie); and

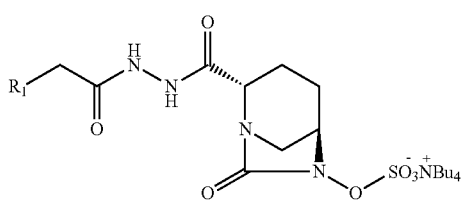

(d) converting a compound of Formula (Ie) to obtain a compound of Formula (I).

palladium on carbon, 20% palladium hydroxide on carbon, in presence of suitable hydrogen source such as hydrogen gas, ammonium formate, or cyclohexene, in presence of a suitable solvent such as methanol, ethanol, methanol-dichloromethane mixture, or N,N-dimethylformamide-dichloromethane mixture, at a temperature ranging from about 25° C. to 60° C. for about 1 to 14 hour to obtain a compound of Formula (Id). In some embodiments, compound of Formula (Ic) is converted to a compound of Formula (Id) in presence of 10% palladium on carbon and hydrogen at a temperature of about 25° C. for about 2 hours.

Scheme-1

In general, compounds of Formula (I), wherein $R_2$ is $SO_3M$, are prepared as described in Scheme-1. Typically, sodium salt of 6-benzyloxy-7-oxo-1,6-diaza-bicyclo[3.2.1]octane-2-carboxylic acid (Ia), is reacted with suitable acid hydrazides (Ib) in presence of a suitable coupling agent such as EDC hydrochloride, HOBt, dicyclohexylcarodiimide (DCC), pivalyl chloride and the like, in suitable solvent such as water, N,N-dimethylformamide, N,N-dimethylacetamide, or 1,4-dioxane, at a temperature ranging from about −15° C. to 60° C. for about 1 hour to 24 hour to obtain a compound of Formula (Ic). In some embodiments, compound of Formula (Ia) is reacted with a compound of Formula (Ib) in presence of EDC hydrochloride and HOBt at a temperature of about 25° C. for about 18 hour to obtain a compound of Formula (Ic).

The compound of Formula (Ic) is subjected to hydrogenolysis in presence of a suitable catalyst such as 5% or 10%

The compound of Formula (Id) is sulfonated by reacting with a suitable sulfonating reagent such as sulfur trioxide-pyridine complex, or sulfur trioxide-N,N-dimethylformamide complex, in presence of a suitable solvent such as pyridine, or N,N-dimethyl formamide, at a temperature ranging from about 25° C. to 90° C. for about 1 to 24 hours to obtain corresponding pyridine salt of sulfonic acid. This is further treated with suitable reagent such as tetrabutylammonium acetate, tetrabutylammonium hydrogen sulfate, tetrabutylammonium sulfate and the like to provide tetrabutylammonium salt of sulfonic acid as a compound of Formula (Ie). In some embodiments, compound of Formula (Id) is sulfonated in presence of sulfur trioxide-pyridine complex at a temperature of about 25° C. for about 1 to 24 hours. The sulphonated compound is further treated with tetrabutylammonium hydrogen sulfate to provide a compound of Formula (Ie).

Some compounds according to invention are isolated as zwitterions, by treating a compound of Formula (Ie) with trifluoroacetic acid, in a suitable solvent such as dichloromethane, chloroform, or acetonitrile, at a temperature ranging from about −15° C. to 40° C. for about 0.5 to 14 hours. In some embodiments, compound of Formula (Ie) is treated with trifluoroacetic acid in presence of dichloromethane at a temperature of about −10° C. for about 0.5 to 14 hours to obtain a compound of Formula (I), wherein $R_2$ is $SO_3M$.

Some other compounds according to the invention are isolated as a corresponding sodium salt, by passing intermediate compound of Formula (Ie) through sodium form of Amberlite 200C resin in a tetrahydrofuran-water mixture followed by evaporation of the solvent under vacuum.

The compounds according to invention wherein $R_2$ is selected from $CF_2COOM$ or $CHFCOOM$ or $CH_2COOM$ were prepared by general reaction scheme as described in Scheme-2. The hydroxyl intermediate (Id) obtained as per Scheme-1, is subjected to alkylation with an alkylating agent (IIa) such as ethyl-bromoacetate, ethyl-bromofluoroacetate, or ethyl-bromodifluoroacetate, in presence of a base such as potassium carbonate, diisopropylethylamine or triethylamine, in a suitable solvent such as N,N-dimethyl formamide, N,N-dimethylacetamide or N-methyl pyrrolidine, to provide 0-alkylated compound (IIb).

The compound of Formula (IIb) is subjected for hydrolysis in presence of a base such as lithium hydroxide or potassium hydroxide, in a suitable solvent such as aqueous tetrahydrofuran or aqueous dioxane, to provide compound of Formula (I). Optionally, if $R_1$ bears amine function protected with Boc group, then it is removed with an additional step of deprotection by using a suitable deprotecting agent (such as trifluoroacetic acid or hydrogen fluoride-pyridine) in a suitable solvent such as dichloromethane, chloroform or acetonitrile, to provide a compound of Formula (I), wherein, $R_2$ is selected from $CF_2COOM$ or $CHFCOOM$ or $CH_2COOM$.

Scheme-2

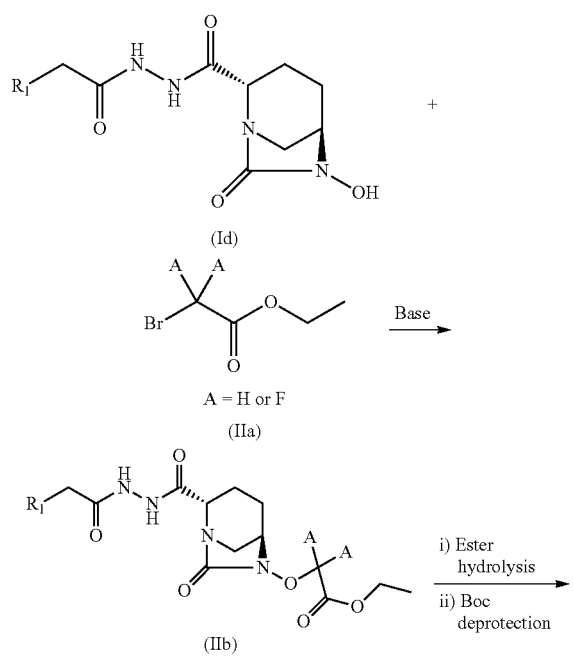

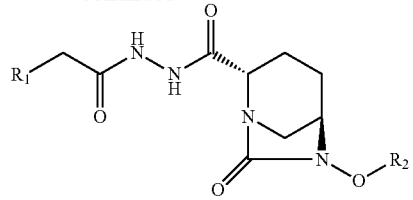

Compound of Formula (I),
wherein $R_2$ is $-CA_2COOH$ and
A is H or F

In some embodiments, there are provided pharmaceutical compositions comprising a compound of Formula (I) or a stereoisomer or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) a compound of Formula (I) or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) a compound of Formula (I) or a stereoisomer or a pharmaceutically acceptable derivative thereof, (b) at least one beta-lactamase inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising a compound of Formula (I) or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I), or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I), or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) a compound of Formula (I) or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject a compound of Formula (I) or a stereoisomer or a pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) a compound of Formula (I) or a stereoisomer or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, there are provided pharmaceutical compositions comprising (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof.

In some other embodiments, there are provided pharmaceutical compositions comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, and (b) at least one beta-lactamase inhibitor or a pharmaceutically acceptable derivative thereof.

In some other embodiments, there are provided pharmaceutical compositions comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, and (b) at least one beta-lactamase inhibitor selected from sulbactam, tazobactam, clavulanic acid, avibactam or a pharmaceutically acceptable derivative thereof.

In some other embodiments, there are provided pharmaceutical compositions comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, and (b) at least one antibacterial agent or a pharmaceutically acceptable derivative thereof.

In some other embodiments, there are provided pharmaceutical compositions comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, and (b) at least one antibacterial agent selected from cefepime, cefpirome, ceftaroline, ceftazidime, ceftalozane or a pharmaceutically acceptable derivative thereof.

In some other embodiments, there are provided pharmaceutical compositions comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, (b) at least one beta-lactamase inhibitor or a pharmaceutically acceptable derivative thereof, and (c) at least one antibacterial agent, or a pharmaceutically acceptable derivative thereof.

In some other embodiments, there are provided methods for preventing or treating a bacterial infection in a subject, said methods comprising administering to said subject a pharmaceutical composition comprising (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof and (b) at least one beta-lactamase inhibitor or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof and (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, and (b) at least one antibacterial agent or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, and (b) at least one antibacterial agent selected from selected from cefepime, cefpirome, ceftaroline, ceftazidime, ceftalozane or a pharmaceutically acceptable derivative thereof.

In some other embodiments, there are provided methods for preventing or treating a bacterial infection in a subject, said methods comprising administering to said subject a pharmaceutical composition comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, (b) at least one beta-lactamase inhibitor or pharmaceutically acceptable derivative thereof and (c) at least one antibacterial agent or a pharmaceutically acceptable derivative thereof.

In some other embodiments, there are provided methods for preventing or treating a bacterial infection in a subject, said method comprising administering to said subject (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof.

In some other embodiments, there are provided methods for preventing or treating a bacterial infection in a subject, said methods comprising administering to said subject: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl} ester or a stereoisomer or a pharmaceutically acceptable derivative thereof, (b) at least one beta-lactamase inhibitor or pharmaceutically acceptable derivative thereof.

In some other embodiments, there are provided methods for preventing or treating a bacterial infection in a subject, said methods comprising administering to said subject: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, (b) at least one beta-lactamase inhibitor selected from sulbactam, tazobactam, clavulanic acid, avibactam, or pharmaceutically acceptable derivative thereof.

In some other embodiments, there are provided methods for preventing or treating a bacterial infection in a subject, said methods comprising administering to said subject: (a) ((2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable derivative thereof, (b) at least one antibacterial agent or pharmaceutically acceptable derivative thereof.

In some other embodiments, there are provided methods for preventing or treating a bacterial infection in a subject, said methods comprising administering to said subject: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a pharmaceutically acceptable derivative thereof, (b) at least one antibacterial agent selected from selected from cefepime, cefpirome, ceftaroline, ceftazidime, ceftalozane or pharmaceutically acceptable derivative thereof.

In some other embodiments, there are provided methods for preventing or treating a bacterial infection in a subject, said methods comprising administering to said subject: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a pharmaceutically acceptable derivative thereof, (b) at least one beta-lactamase inhibitor or pharmaceutically acceptable derivative thereof, and (c) at least one antibacterial agent or pharmaceutically acceptable derivative thereof.

In some embodiments, the compositions and methods according to the invention use compounds of Formula (I) or a stereoisomer or a pharmaceutically acceptable derivative thereof, in combination with at least one antibacterial agent. A wide variety of antibacterial agents can be used. Typical, non-limiting examples of antibacterial agents include one or more of antibacterial compounds generally classified as aminoglycosides, ansamycins, carbacephems, cephalosporins, cephamycins, lincosamides, lipopeptides, macrolides, monobactams, nitrofurans, penicillins, polypeptides, quinolones, sulfonamides, tetracyclines, oxazolidinone and the like. Typical, non-limiting examples of aminoglyco side antibacterial agents include amikacin, gentamicin, kanamycin, neomycin, netilmicin, tobramycin, paromomycin, arbekacin, streptomycin, apramycin and the like. Typical, non-limiting examples of ansamycin antibacterial agents include geldanamycin, herbimycin and the like. Typical, non-limiting examples of carbacephem antibacterial agents include loracarbef and the like. Typical, non-limiting examples of carbapenam antibacterial agents include ertapenem, doripenem, imipenem, meropenem and the like.

Typical, non-limiting examples of cephalosporin and cephamycin antibacterial agents include cefazolin, cefacetrile, cefadroxil, cefalexin, cefaloglycin, cefalonium, cefaloridine, cefalotin, cefapirin, cefatrizine, cefazedone, cefazaflur, cefradine, cefroxadine, ceftezole, cefaclor, cefamandole, cefminox, cefonicid, ceforanide, cefotiam, cefprozil, cefbuperazone, cefuroxime, cefuzonam, cephamycin, cefoxitin, cefotetan, cefmetazole, carbacephem, cefixime, ceftazidime, ceftriaxone, cefcapene, cefdaloxime, cefdinir, cefditoren, cefetamet, cefmenoxime, cefodizime, cefoperazone, cefotaxime, cefpimizole, cefpiramide, cefpodoxime, cefsulodin, cefteram, ceftibuten, cefiolene, ceftizoxime, oxacephem, cefepime, cefozopran, cefpirome, cefquinome, ceftobiprole, cetiofur, cefquinome, cefovecin, CXA-101, ceftaroline, ceftobiprole, cefoselis, cefluprenam, cefclidin, loracarbacef, ceftolozane, latamoxef and the like.

Typical, non-limiting examples of lincosamide antibacterial agents include clindamycin, lincomycin and the like. Typical, non-limiting examples of macrolide antibacterial agents include azithromycin, clarithromycin, dirithromycin, erythromycin, roxithromycin, troleandomycin, telithromycin, spectinomycin and the like. Typical, non-limiting examples of monobactam antibacterial agents include aztreonam and the like. Typical, non-limiting examples of nitrofuran antibacterial agents include furazolidone, nitrofurantoin and the like. Typical, non-limiting examples of penicillin antibacterial agents include amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, colistin, polymyxin B and the like.

Typical, non-limiting examples of polypeptide antibacterial agents include bacitracin, colistin, polymyxin B and the like. Typical, non-limiting examples of quinolone antibacterial agents include ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin and the like. Typical, non-limiting examples of sulfonamide antibacterial agents include mafenide, sulfonamidochrysoidine, sulfacetamide, sulfadiazine, sulfamethizole, sulfamethoxazole, sulfasalazine, sulfisoxazole, trimethoprim and the like. Typical, non-limiting examples of tetracycline antibacterial agents include demeclocycline, doxycycline, minocycline, oxytetracycline, tetracycline, tigecycline and the like. Typical non-limiting examples of oxazolidinone anti-bacterial agents include linezolid, ranbezolid, torezolid, radezolid and the like. Typical non-limiting examples of beta-lactamase inhibitor include sulbactam, tazobactam, clavulanic acid, avibactam and the like.

The pharmaceutical compositions according to the invention may include one or more pharmaceutically acceptable carriers or excipients or the like. Typical, non-limiting examples of such carriers or excipients include mannitol, lactose, starch, magnesium stearate, sodium saccharine, talcum, cellulose, sodium crosscarmellose, glucose, gelatin, sucrose, magnesium carbonate, wetting agents, emulsifying agents, solubilizing agents, pH buffering agents, lubricants, preservatives, stabilizing agents, binding agents etc.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for oral or parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and the nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intrarespiratory, intraperitoneal, intramuscular, parenteral, sublingual, transdermal, intranasal, aerosol, intraocular, intratracheal, intrarectal, vaginal, gene gun, dermal patch, eye drop, ear drop or mouthwash. In some embodiments, compounds and compositions according to invention are administered orally or parenterally.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered separately, the invention further provides for combining separate pharmaceutical compositions in kit form. The kit may comprise one or more separate pharmaceutical compositions, each comprising one or more active ingredients. Each of such separate compositions may be present in a separate container such as bottle, vial, syringes, boxes, bags, and the like. Typically, the kit comprises directions for the administration of the separate components. The kit form is particularly advantageous when the separate components are preferably administered in different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the pharmaceutical compositions and method disclosed herein are useful in preventing or treating bacterial infections. Advantageously, the compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be prevented or treated using the compositions and/or methods of the invention include: skin and soft tissue infections, febrile neutropenia, urinary tract infection, intraabdominal infections, respiratory tract infections, pneumonia (nosocomial), bacteremia meningitis, surgical, infections etc.

Surprisingly, the compounds, pharmaceutical compositions and methods according to the invention are useful in treatment or prevention of infections caused by resistant bacteria. The compounds, compositions and methods according to the invention are also useful in treatment or prevention of infections caused by bacteria producing one or more beta-lactamase enzymes including those producing extended spectrum beta-lactamase enzymes.

In some embodiments, there are provided methods for preventing or treating a bacterial infection in a subject, said infection being caused by bacteria producing one or more beta-lactamase enzymes, said methods comprising administering to said subject a compound of Formula (I). In some other embodiments, there are provided methods for preventing or treating a bacterial infection in a subject, said infection being caused by bacteria producing one or more beta-lactamase enzymes, said methods comprising administering to said subject a pharmaceutical composition comprising compound of Formula (I).

In general, the compounds of Formula (I) or a stereoisomer or pharmaceutically acceptable derivative thereof according to invention are also useful in increasing antibacterial effectiveness of an antibacterial agent in a subject. The antibacterial effectiveness of one or more antibacterial agents may be increased, for example, by co-administering said antibacterial agents or a pharmaceutically acceptable derivative thereof with a compound of Formula (I) or a stereoisomer or a pharmaceutically acceptable derivative thereof according to the invention. In some other embodiments, there are provided methods for increasing antibacterial effectiveness of an antibacterial agent in a subject, said methods comprising co-administering said antibacterial agent or a pharmaceutically acceptable derivative thereof with a compound of Formula (I) or a stereoisomer or a pharmaceutically acceptable derivative thereof.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods and systems may be devised by those skilled in the art without departing from the spirit and scope of the present invention. The appended claims are intended to cover such modifications and arrangements. Thus, while the present invention has been described above with particularity, the following examples provide further detail in connection with what is presently deemed to be the most practical and preferred embodiments of the invention.

Example-1

Synthesis of (2S,5R)-Sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester

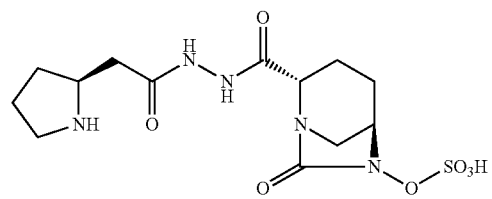 [SMILES: O=C(C[C@@H]1CCCN1)NNC(=O)[C@@H]1CC[C@@H]2CN1C(=O)N2OS(=O)(=O)O]

Step-1: Preparation of (2S,5R)-2-{N'-[2-(S)—N-tert-butoxycarbonyl-pyrrolidin-2-yl-acetyl]-hydrazinocarbonyl}-6-benzyloxy-7-oxo-1,6-diaza-bicyclo[3.2.1]octane To a clear solution of sodium salt of (2S,5R)-6-benzyloxy-7-oxo-1,6-diaza-bicyclo[3.2.1]octane-2-carboxylic acid (31.5 g, 0.106 mol) (prepared according to the process disclosed in PCT/IB2013/059264) in water (500 ml), was added EDC hydrochloride (30.4 g, 0.159 mol), followed by HOBt (14.3 gm, 0.106 mol) at about 25° C. under stirring. The reaction mixture was stirred for 15 minutes and a solution of (S)-(N-tert-butoxycarbonyl-pyrrolidin-2-yl)-acetic acid hydrazide (26 g, 0.106 mol) dissolved in water (150 ml) was added. The reaction mixture was stirred at 25° C. for 18 hour. The precipitated solid was filtered, washed with water (650 ml) and dried under reduced pressure. The residue was suspended in water (650 ml) and stirred at 45° C. for 3 hour. The reaction mixture was filtered and the solid was washed with water (650 ml). The solid was dried under reduced pressure and dissolved in dichloromethane (1000 ml). The organic layer was dried over anhydrous sodium sulphate, filtered and evaporated to obtain 40 g of (2S,5R)-[2-(N'—[(S)—N-tert-butoxycarbonyl-pyrrolidin-2-yl-methylcarbonyl]-hydrazinocarbonyl)-6-benzyloxy-7-oxo-1,6-diaza-bicyclo[3.2.1]octane, in 75% yield.

Analysis:

Mass: 502.4 (M+1), for Molecular Formula of $C_{25}H_{35}N_5O_6$;

$^1$H NMR (DMSO-d$_6$): δ 9.89 (br d, 2H), 7.33-7.44 (m, 5H), 4.90-4.96 (m, 2H), 3.92-3.96 (m, 1H), 3.80 (d, 1H), 3.69 (s, 1H), 3.26 (s, 2H), 3.23 (d, 1H), 2.90 (d, 1H), 1.99-2.11 (m, 2H), 1.60-1.95 (m, 8H), 1.38 (s, 9H).

Step-2: Preparation of (2S,5R)-2-{N'-[2-(S)—N-tert-butoxycarbonyl-pyrrolidin-2-yl-acetyl]-hydrazinocarbonyl}-6-hydroxy-7-oxo-1,6-diaza-bicyclo[3.2.1]octane To a clear solution of (2S,5R)-[2-(N'—[(S)—N-tert-butoxycarbonyl-pyrrolidin-2-yl-methylcarbonyl]-hydrazinocarbonyl)-6-benzyloxy-7-oxo-1,6-diaza-bicyclo[3.2.1]octane (30 g, 0.0598 mol) in methanol (250 ml), 10% palladium on carbon (3 gm) was added at 25° C. The reaction mixture was stirred under 150 psi hydrogen pressure at 25° C. for 2 hour. The catalyst was filtered under suction over a celite bed. The bed was washed with methanol (125 ml). The combined filtrate was evaporated under vacuum below 35° C. to provide 24.5 g of (2S,5R)-[2-(N'—

[(S)—N-tert-butoxycarbonyl-pyrrolidin-2-yl-methylcarbonyl]-hydrazinocarbonyl)-6-hydroxy-7-oxo-1,6-diaza-bicyclo[3.2.1]octane, in 99% yield. It was used as such for further reaction.

Analysis:

Mass: 410.3 (M−1), for Molecular Formula of $C_{18}H_{29}N_5O_6$;

$^1H$ NMR (DMSO-$d_6$): δ 9.76 (br s, 2H), 3.90-3.97 (m, 1H), 3.75 (d, 1H), 3.60 (s, 1H), 3.30 (s, 2H), 3.19 (d, 1H), 2.97 (d, 1H), 2.00-2.17 (m, 2H), 1.50-1.88 9m, 8H), 1.38 (s, 9H).

Step-3: Preparation of tetrabutyl ammonium salt of (2S,5R)-2-{N'-[2-(S)—N-tert-butoxycarbonyl-pyrrolidin-2-yl-acetyl]-hydrazinocarbonyl}-6-sulphooxy-7-oxo-1,6-diaza-bicyclo[3.2.1]octane To a 1 L single neck round bottom flask equipped with magnetic stirrer was charged a solution of (2S,5R)-[2-(N'—[(S)—N-tert-butoxycarbonyl-pyrrolidin-2-yl-methylcarbonyl]-hydrazinocarbonyl)-6-hydroxy-7-oxo-1,6-diaza-bicyclo[3.2.1]octane (24.5 g, 0.0596 mol) in dichloromethane (250 ml), followed by triethylamine (25 nil, 0.178 mol) and pyridine sulfur trioxide complex (19 gm, 0.119 mol) under stirring. The reaction mixture was stirred for 2 hours at 25° C. The solvent was evaporated under vacuum below 40° C. to provide a residue which was stirred in 0.5 N aqueous potassium dihydrogen phosphate solution (500 ml) for 1 hour. The resulting solution was extracted successively with ethyl acetate (500 ml) and a mixture of ethyl acetate (250 ml) and dichloromethane (125 ml). To the aqueous layer was added tetrabutyl ammonium hydrogen sulfate (18.21 gm, 0.0536 mol) and the mixture was stirred for 15 hour at 25° C. The precipitated solid was filtered under reduced pressure and dried under vacuum to provide 25 g of tetrabutyl ammonium salt of (2S,5R)-[2-(N'—[(S)—N-tert-butoxycarbonyl-pyrrolidin-2-yl-methylcarbonyl]-hydrazinocarbonyl)-6-sulfooxy-7-oxo-1,6-diaza-bicyclo[3.2.1]octane, in 57% yield.

Analysis:

Mass: 490.3 (M−1) as a free sulfonic acid, for Molecular Formula of $C_{18}H_{29}N_5O_9S$. $N(C_4H_9)_4$;

$^1H$ NMR (CDCl$_3$): δ 8.70 (s, 1H), 8.54 (s, 1H), 4.30 (br s, 1H), 4.09-4.15 (m, 1H), 3.97 (d, 1H), 3.23-3.40 (m, 10H), 3.16 (d, 1H), 2.73-2.81 (m, 1H), 2.28-2.42 (m, 2H), 2.10-2.20 (m, 1H), 1.98-2.09 (m, 1H), 1.75-1.96 (m, 7H), 1.57-1.73 (m, 8H), 1.45-1.52 (m, 16H), 0.99 (t, 12H).

Step-4: Preparation of (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester To a 250 ml round bottom flask equipped with magnetic stirrer was charged a solution of tetrabutyl ammonium salt of (2S,5R)-[2-(N'—[(S)—N-tert-butoxycarbonyl-pyrrolidin-2-yl-methylcarbonyl]-hydrazinocarbonyl)-6-sulfooxy-7-oxo-1,6-diaza-bicyclo[3.2.1]octane (24 g, 0.033 mol) in dichloromethane (60 ml). The solution was cooled to −10° C. under stirring and to it was added trifluoroacetic acid (60 ml) drop wise. The reaction mixture was stirred at −10° C. for 2 hour. Solvents were evaporated under vacuum and the residue was taken in diethyl ether (360 ml) and stirred for 1 hour. The mixture was filtered; the solid was washed with diethyl ether (120 ml) and dried under reduced pressure. Acetone (360 ml) was added to the solid and the pH of the solution was adjusted from initial pH 3 to pH 6.5 by addition of 10% solution of sodium 2-ethyl hexanoate in acetone. The reaction mixture was filtered; the solid was washed with acetone (120 ml) and dried under reduced pressure. The solid (13 g) was dissolved in water (13 ml) and 2-propanal (91 ml) was added under stirring. The reaction mixture was stirred for 18 hour, filtered and the solid was washed with a mixture of water (6.5 ml) and 2-propanol (45.5 ml). The solid was dried under reduced pressure to obtain 10.2 g of compound of invention as (2S,5R)-sulfuric acid mono-[2-(N'—[(S)-pyrrolidin-2-yl-methylcarbonyl]-hydrazinocarbonyl)-7-oxo-1,6-diaza-bicyclo[3.2.1]oct-6-yl]ester in 79% yield.

Analysis:

Mass: 390.1 (M−1), for Molecular Formula of $C_{13}H_{21}N_5O_7S$;

$^1H$ NMR (DMSO-d6, D2O exchange): δ 4.00 (br s, 1H), 3.83 (d, 1H), 3.60-3.66 (m, 1H), 3.17 (d, 1H), 3.10 (t, 2H), 2.90-3.07 (m, 1H), 2.53-2.64 (m, 2H), 1.98-2.11 9m, 2H), 1.67-1.89 (m, 4H), 1.50-1.62 (m, 2H).

Compounds 2 to 7 (Table 1) were prepared using the procedure described in Example-1 and using corresponding $R1CH_2$—$CONHNH_2$, in the place of (S)-(N-tert-butoxycarbonyl-pyrrolidin-2-yl)-acetic acid hydrazide.

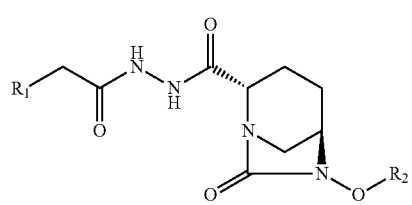

Formula (I)

TABLE 1

| Example No. | $R1CH_2$—$CONHNH_2$ (Acid hydrazide) | R1 | $^1H$ NMR | Mass (Molecular Formula) |
|---|---|---|---|---|
| 2. | boc—N⟨⟩—$CH_2CONHNH_2$ | HN⟨⟩— | (DMSO-d6): δ 9.82 (d, 2H), 8.54 (br s, 1H), 8.38 (br s, 1H), 3.97-4.00 (m, 3H), 3.75-3.80 (m, 3H), 2.53-3.19 (m, 5H), 1.98-2.03 (m, 1H), 1.82-1.87 (m, 1H), 1.66-1.76 (m, 1H), 1.52-1.62 (m, 1H). | 376.2 (M − 1) ($C_{12}H_{19}N_5O_7S$) |
| 3. | (piperidine-boc)-$CH_2CONHNH_2$ | (piperidine-NH)— | (DMSO-d6): δ 10.03 (s, 1H), 9.96 (s, 1H), 8.45 (br d, 1H), 8.23 (br d, 1H), 4.01 (s, 1H), 3.84 (d, 1H), 3.30-3.52 (m, 3H), 3.24 (d, 1H), 3.17 (d, 1H), 3.00 (d, 1H), 2.92 (d, 1H), 2.00-2.05 (m, 1H), 1.71-1.89 (m, 2H), 1.68-1.70 (m, 2H), 1.57-1.62 (m, 1H), 1.33-1.49 (m, 4H). | 404.2 (M − 1); ($C_{14}H_{23}N_5O_7S$) |

TABLE 1-continued

| Example No. | R1CH₂—CONHNH₂ (Acid hydrazide) | R1 | $^1$H NMR | Mass (Molecular Formula) |
|---|---|---|---|---|
| 4. | (piperidine-N-boc, 2-CH₂CONHNH₂) | (piperidine-NH, 2-position) | (DMSO-d6): δ 10.06 (s, 1H), 9.97 (s, 1H), 8.40 (br s, 1H), 8.25 (br s, 1H), 4.01 (s, 1H), 3.82 (d, 1H), 3.32-3.40 (m, 1H), 3.21-3.28 (m, 1H), 3.17 (d, 1H), 2.99-3.03 (m, 1H), 2.87-2.94 (m, 1H), 2.40-2.50 (m, 2H), 1.97-2.03 (m, 1H), 1.73-1.85 (m, 1H), 1.64-1.72 (m, 2H), 1.35-1.62 (m, 6H). | 404.4 (M − 1); (C₁₄H₂₃N₅O₇S) |
| 5. | (piperidine-N-boc, 3-CH₂CONHNH₂) | (piperidine-NH, 3-position) | (DMSO-d6): δ 9.89 (s, 1H), 9.78 (s, 1H), 8.45 (br s, 1H), 8.30 (br s, 1H), 4.01 (s, 1H), 3.81 (d, 1H), 3.23-3.40 (m, 4H), 3.20 (d, 1H), 2.95-3.05 (m, 1H), 1.95-2.14 (m, 7H), 1.68-1.92 (m, 2H), 1.53-1.65 (m, 2H). | 404.2 (M − 1); (C₁₄H₂₃N₅O₇S) |
| 6. | (piperidine-N-boc, 4-CH₂CONHNH₂) | (piperidine-NH, 4-position) | (DMSO-d6); δ 9.88 (s, 1H), 9.78 (s, 1H), 8.40 (br s, 1H), 8.06 (br s, 1H), 4.00 (s, 1H), 3.80 (d, 1H), 3.20-3.26 (m, 4H), 3.24-3.28 (m, 1H), 2.99 (d, 1H), 2.80-2.91 (m, 2H), 1.93-2.02 (m, 3H), 1.83-1.89 (m, 2H), 1.52-1.72 (m, 2H), 1.25-1.34 (m, 2H). | 404.3 (M − 1); C₁₄H₂₃N₅O₇S. |
| 7. | (piperazine-N,N'-bis-boc, CH₂CONHNH₂) | (piperazine-NH,NH) | (DMSO-d6): δ 10.13 (s, 1H), 10.00 (d, 1H), 9.02 (br s, 3H), 4.02 (s, 1H), 3.85 (d, 1H), 3.61-3.55 (m, 2H), 2.93-3.36 (m, 6H), 2.57-2.65 (m, 3H), 1.99-2.02 (m, 1H), 1.85-1.89 (m, 1H), 1.69-1.75 (m, 1H), 1.54-1.58 (m, 1H). | 405.2 (M − 1) as a free sulfonic acid; (C₁₃H₂₃N₆O₇S·C₂O₂F₃) |

Biological Activity Data

The biological activity of representative compounds according to the invention against various bacterial strains was investigated. In a typical study, overnight grown bacterial cultures were diluted appropriately and inoculated on the agar media containing doubling dilutions of the test compounds. Observations for growth or no growth was performed after 16-20 hours of incubation at 35±2° C. in the ambient air. The overall procedure was performed as per Clinical and Laboratory Standards Institute (CLSI) recommendations, (Clinical and Laboratory Standards Institute (CLSI), Performance Standards for Antimicrobial Susceptibility Testing, 20$^{th}$ Informational Supplement, M07-A9, Volume 32, No. 2, 2012). Molten Mueller Hinton Agar (BD, USA) containing serial dilutions of each antibacterial agent were poured on to the plates and allowed to solidify. Appropriate suspensions from the freshly grown cultures were prepared in normal saline so that about 10$^4$ CFU/spot of the organism was delivered on to the drug containing agar plates using automated multipoint inoculator (Mast, UK). The plates were incubated in Biochemical oxygen demand (BOD) incubator at 37° C. for 18 hours and then examined for growth.

Table 2 details the antibacterial activity of representative compounds according to invention, against various Multi Drug Resistant (MDR) Gram-negative bacterial strains. The strains selected for study included *E. coli* NCTC 13353 producing CTX-M15 and OXA-1 beta-lactamase enzymes; *K. pneumoniae* H521 producing KPC, SHV, TEM beta-lactamase enzymes; and *K. pneumoniae* S48 producing NDM, SHV, TEM beta-lactamase enzymes. The activities are expressed as Minimum Inhibitory Concentrations (MICs) (mcg/ml). The antibacterial activity profile of representative compounds according to invention were compared against known antibacterial agent such as imipenem and ceftazidime. As can be seen, the MIC values for the compounds of Formula (I) were much lower in comparison to the standards (imipenem and ceftazidime). Therefore, the results of Table 2 suggests that the compounds of invention exhibited good antibacterial activity against the multidrug resistant gram negative strains.

TABLE 2

Antibacterial activity of representative compounds according to invention (expressed as MICs (mcg/ml)).

| Compounds | *E. Coli* NCTC 13353 (CTX-M15, OXA-1) | *K. pneumoniae* H521 (KPC, SHV, TEM) | *K. pneomoniae* S48 (NDM, SHV, TEM) |
|---|---|---|---|
| Imipenem | 0.25 | 16 | 16 |
| Ceftazidime | 32 | >32 | >32 |
| Example 1 | 0.5 | 0.5 | 0.5 |
| Example 2 | 1 | 4 | 2 |
| Example 3 | 0.25 | 0.5 | 0.5 |
| Example 4 | 2 | 4 | 2 |
| Example 5 | 0.5 | 4 | 1 |
| Example 6 | 0.5 | 2 | 1 |
| Example 7 | 2 | 4 | 2 |

Table 3 details the antibacterial activity of representative compound of Formula (I), (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester (Compound of Example 1), against various Multi Drug Resistant (MDR) Gram-negative bacterial strains. The activities are expressed as Minimum Inhibitory Concentrations (MICs) (mcg/ml). As can be seen in Table 3, the MIC values obtained for compound of Example No. 1 were found to be lower than those obtained for avibactam. Hence, (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester (compound of Example No. 1) exhibited good antibacterial activity against various Multi Drug Resistant (MDR) Gram-negative bacterial strains.

TABLE 3

Antibacterial activity of (2S,5R)-sulfuric acid mono-{2-N'-(2-(S)-pyrrolidin-2-yl-acetyl)-hydrazinocarbonyl]-7-oxo-1,6-diaza-bicyclo[3.2.1] oct-6-yl} ester (Compound of Example No. 1) against various Gram negative bacterial strains.

| Organism | MIC (mcg/ml) | |
| --- | --- | --- |
| | Compound of Example 1 | Avibactam |
| E. coli NCTC 13351 | 0.5 | >64 |
| E. coli NCTC 13352 | 0.5 | >64 |
| E. coli NCTC 13353 | 0.5 | 16 |
| E. coli M 49 | 2 | 16 |
| E. coli M 50 | 0.5 | >64 |
| E. coli 7 MP | 1 | >64 |
| C. frundaii 58 MP | 0.5 | >64 |
| E. cloacae M 20 | 0.5 | >64 |
| K. pneumoniae H 521 | 0.5 | 16 |
| K. pneumoniae H 525 | 0.5 | 8 |
| K. pneumoniae B 88 | 0.5 | 32 |
| K. pneumoniae S 21 | 2 | 16 |
| P. aeruginosa PAO1 | 4 | >64 |
| P. aeruginosa ATCC 27853 | 8 | >64 |
| P. aeruginosa R 20 | 16 | >64 |
| P. aeruginosa 2779 | 8 | >64 |

Determination of Enzyme Inhibition Activity:

$IC_{50}$ is concentration of the compound required to inhibit 50% of enzymatic activity. $IC_{50}$ values for various compounds was measured by adding Nitrocefin (100 μM, 5 min) to the preincubated mixture of crude enzyme and the compounds (37° C., 10 minutes). Absorbance was measured at 485 nm by UV-spectrophotometer. The $IC_{50}$ was calculated by plotting absorbance against concentration through Sigmoidal dose response curve using Graph Pad software.

The Table 4 provides the beta-lactamase enzyme inhibition activity of representative compounds of Formula (I), against Multi Drug Resistant Gram-negative bacterial strains expressing various ESBLs. The enzyme inhibition was expressed as $IC_{50}$. As can be seen from the data of Table 4, the beta-lactamase enzyme inhibition values for the compounds according to invention were found to be lower than avibactam and clavulanic acid. The compounds according to invention exhibited potent antibacterial activity against wide variety of bacteria producing Class A, Class C and Class D types of beta-lactamase enzymes. Surprisingly, the representative compounds according to invention exhibit even better than avibactam and clavulanic acid.

TABLE 4

Beta-lactamase enzyme inhibition activity of representative compounds according to invention (expressed as $IC_{50}$ (μM))

| Compound | Class A K. pneumoniae ATCC 700603 (SHV 18) | Class C E. coli M50 (CMY/DHA) | Class D A. baumannii NCTC 13301 (OXA 23) |
| --- | --- | --- | --- |
| Avibactam | 0.098 | 0.146 | 9.735 |
| Clavulanic acid | 0.021 | >10 | >10 |
| Example 1 | 0.08 | 0.06 | 2.389 |
| Example 2 | 0.097 | 0.103 | 6.187 |
| Example 3 | 0.074 | 0.052 | 2.111 |
| Example 4 | 0.170 | 0.056 | 2.93 |
| Example 5 | 0.16 | 0.03 | 1.73 |

TABLE 4-continued

Beta-lactamase enzyme inhibition activity of representative compounds according to invention (expressed as $IC_{50}$ (μM))

| Compound | Class A K. pneumoniae ATCC 700603 (SHV 18) | Class C E. coli M50 (CMY/DHA) | Class D A. baumannii NCTC 13301 (OXA 23) |
| --- | --- | --- | --- |
| Example 6 | 0.06 | 0.037 | 1.615 |
| Example 7 | 0.067 | 0.070 | 2.842 |

The Table 5 provides the beta-lactamase enzyme inhibition activity of (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester (compound of Example 1), against Multi Drug Resistant Gram-negative bacterial strains expressing various ESBLs. As can be seen from the data of Table 5, the $IC_{50}$ values obtained for compound of Example 1 were significantly lower than those obtained for avibactam and clavulanic acid. The compound of Example 1 exhibited potent antibacterial activity against wide variety of bacterial strains producing different types of beta-lactamase enzymes including those of Class A, Class C and Class D.

TABLE 5

Beta-lactamase enzyme inhibition activity of (2S,5R)-sulfuric acid mono-{2-N'-(2-(S)-pyrrolidin-2-yl-acetyl)-hydrazinocarbonyl]-7-oxo-1,6-diaza-bicyclo[3.2.1] oct-6-yl} ester (Compound of Example 1) against bacterial strains producing ESBLs

| Organism | ESBL Class | ESBL type | $IC_{50}$ (μM) | | |
| --- | --- | --- | --- | --- | --- |
| | | | Avibactam | Clavulanic Acid | Compound of Example 1 |
| K. pneumoniae ATCC 700603 | Class A | SHV 18 | 0.010 | 0.021 | 0.081 |
| E. coli M50 | Class C | CMY/DHA | 0.146 | >10 | 0.065 |
| E. cloacae J137 | Class C | P99 | 0.079 | >10 | 0.027 |
| A. baumannii NCTC 13301 | Class D | OXA 23 | 11.95 | >10 | 2.389 |
| A. baumannii NCTC 13303 | Class D | OXA 26 | 10.07 | >10 | 4.767 |

Determination of Antibacterial Activity of Combinations According to Invention:

In a typical experiment, two sets of plates containing growth media (Molten Mueller Hilton Agar) and bacterial strains were prepared. One set of plates was taken as control (without ceftazidime) and other set contained ceftazidime. The media was allowed to solidify and wells were punched later, into which varying concentrations of compounds according to the invention were poured. A two-fold serial dilution range of each of the compounds according to invention was prepared and 50 μl of each of the dilution was added into the punched well. The plates were then incubated at 37° C. for 18 hours in BOD incubator and diameters of zone of inhibition were measured after the completion of the incubation.

TABLE 6

Antibacterial activity of combination comprising
compounds according to invention and Ceftazidime.

| Compounds of Formula (I) | Concentrations (μg/well) | Diameter of Zone of Inhibition (mm) | | | |
|---|---|---|---|---|---|
| | | E. coli NCTC 13353 | | E. coli M50 | |
| | | Compound | Compound + Ceftazidime (10 μg/ml) | Compound | Compound + Ceftazidime (10 μg/ml) |
| Example 1 | 0.12 | 11.5 | 22 | 10.5 | 17 |
| | 0.25 | 14 | 26 | 14 | 19 |
| | 0.5 | 15 | 28 | 16 | 20.5 |
| | 1 | 16.5 | 31 | 18 | 22.5 |
| Example 2 | 0.12 | No growth | 21 | No growth | 15 |
| | 0.25 | 10 | 24 | 9 | 19 |
| | 0.5 | 13 | 26 | 12 | 22 |
| | 1 | 15 | 30 | 15 | 23.5 |
| Example 3 | 0.12 | 11 | 20 | 11 | 14.5 |
| | 0.25 | 14 | 22 | 13 | 17.5 |
| | 0.5 | 15 | 27 | 16 | 20 |
| | 1 | 17 | 30 | 17 | 22.5 |

The Table 6 provides the antibacterial activity of the combination comprising compounds according to invention and ceftazidime. The compounds according to invention were tested at 0.12, 0.25, 0.5 and 1 μg/well. As can be seen from the results of the Table 6 the diameter to zone of inhibition significantly increased in presence of ceftazidime. The compounds according to invention exhibited synergistic antibacterial activity in presence of ceftazidime.

The results of Tables 1 to 6 clearly demonstrate potent antibacterial activity of compounds according to invention, even against highly resistant gram negative bacteria producing ESBLs. Thus, the compounds of Formula (I) has tremendous beneficial effect in inhibiting highly resistant bacterial strains demonstrating the noteworthy therapeutic advance in the treatment of infections caused by such pathogens.

The invention claimed is:

1. A compound wherein said compound is selected from:
   (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester;
   (2S,5R)-sulfuric acid mono-{2-[N'-(2-azetidin-3-yl-acetyl)-hydrazinocarbonyl]-7-oxo-1,6-diaza-bicyclo[3.2.1]oct-6-yl}ester;
   (2S,5R)-sulfuric acid mono-{2-[N'-(2-(S)-piperidin-2-yl-acetyl)-hydrazinocarbonyl]-7-oxo-1,6-diaza-bicyclo[3.2.1]oct-6-yl}ester;
   (2S,5R)-sulfuric acid mono-{2-[N'-(2-(R)-piperidin-2-yl-acetyl)-hydrazinocarbonyl]-7-oxo-1,6-diaza-bicyclo[3.2.1]oct-6-yl}ester;
   (2S,5R)-sulfuric acid mono-{2-[N'-(2-(S)-piperidin-3-yl-acetyl)-hydrazinocarbonyl]-7-oxo-1,6-diaza-bicyclo[3.2.1]oct-6-yl}ester;
   (2S,5R)-sulfuric acid mono-{2-[N'-(2-(RS)-piperazin-2-yl-acetyl)-hydrazinocarbonyl]-7-oxo-1,6-diaza-bicyclo[3.2.1]oct-6-yl}ester;
   or a stereoisomer or a pharmaceutically acceptable salt thereof.

2. A pharmaceutical composition comprising the compound according to claim 1.

3. The pharmaceutical composition according to claim 2, wherein the compound is (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester or a stereoisomer or a pharmaceutically acceptable salt thereof.

4. The pharmaceutical composition according to claim 2, further comprising at least one beta-lactamase inhibitor, or a pharmaceutically acceptable salt thereof.

5. The pharmaceutical composition according to claim 4, wherein the beta-lactamase inhibitor is selected from the group consisting of sulbactam, tazobactam, clavulanic acid, avibactam, and a pharmaceutically acceptable salt thereof.

6. The pharmaceutical composition according to claim 2, further comprising at least one antibacterial agent or a pharmaceutically acceptable salt thereof.

7. The pharmaceutical composition according to claim 6, wherein the antibacterial agent is selected from a group consisting of aminoglycosides, ansamycins, carbacephems, cephalosporins, cephamycins, lincosamides, lipopeptides, macrolides, monobactams, nitrofurans, penicillins, penems, carbapenems, polypeptides, quinolones, sulfonamides, tetracyclines, oxazolidinones, and beta-lactam antibacterial agents.

8. The pharmaceutical composition according to claim 6, wherein the antibacterial agent is a cephalosporin antibiotic, wherein the cephalosporin antibiotic is selected from the group consisting of cephalotin, cephaloridine, cefaclor, cefadroxil, cefamandole, cefazolin, cefalexin, cefradine, ceftizoxime, cefoxitin, cephacetrile, cefotiam, cefotaxime, cefsulodin, cefoperazone, cefmenoxime, cefmetazole, cepfaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidin, cefixime, ceftibuten, cefdinir, cefpodoxime auxetil, cefpodoxime proxetil, cefteram pivoxil, cefetamet pivoxil, cefcapene pivoxil, cefditoren pivoxel, cefuroxime, cefuroxime auxetil, loracarbacef, ceftaroline, ceftolozane, and latamoxef.

9. The pharmaceutical composition according to claim 4, comprising (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester, or a stereoisomer, or a pharmaceutically acceptable salt thereof, and (b) sulbactam, or a pharmaceutically acceptable salt thereof.

10. The pharmaceutical composition according to claim 6, comprising: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester, and (b) at least one antibacterial agent selected from cefepime, cefpirome, ceftaroline, ceftazidime, ceftalozane, or a pharmaceutically acceptable salt thereof.

11. A method for treating a bacterial infection in a subject, the method comprising administering to the subject the compound according to claim 1.

12. A method for treating a bacterial infection in a subject, the method comprising administering to the subject: (a) the compound according to claim 1, and (b) at least one beta-lactamase inhibitor or a pharmaceutically acceptable salt thereof.

13. A method for treating a bacterial infection in a subject, the method comprising administering to the subject: (a) the compound according to claim 1, and (b) at least one antibacterial agent or a pharmaceutically acceptable salt thereof.

14. The method for treating a bacterial infection in a subject according to claim 11, wherein the method comprises administering to the subject (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester, or a stereoisomer or a pharmaceutically acceptable salt thereof.

15. The method for treating a bacterial infection in a subject according to claim 12, wherein the method comprises administering to the subject: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester, or a stereoisomer, or a pharmaceutically acceptable salt thereof, and (b) sulbactam, or a pharmaceutically acceptable salt thereof.

16. The method for treating a bacterial infection in a subject according to claim 13, wherein the method comprises administering to said subject: (a) (2S,5R)-sulfuric acid mono-{2-[N'-(2-(S)-pyrrolidin-2-yl-acetyl)-hydrazinocarbonyl]-7-oxo-1,6-diaza-bicyclo[3.2.1]oct-6-yl}ester, or a stereoisomer or a pharmaceutically acceptable salt thereof, and (b) at least one antibacterial agent selected from cefepime, cefpirome, ceftaroline, ceftazidime, ceftolozane, or a pharmaceutically acceptable salt thereof.

17. A process for the preparation of a compound of Formula (I),

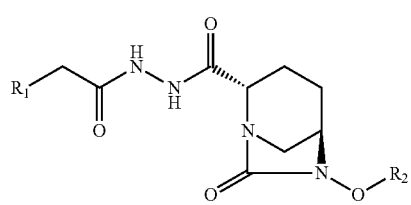

Formula (I)

wherein,
$R_1$ is:
  (a) cycloalkyl optionally substituted with one or more substituents independently
      selected from $C_1$-$C_6$ alkyl, halogen, CN, $OR_3$, $NR_3R_4$, or $CONR_3R_4$, or
  (b) heterocycloalkyl optionally substituted with one or more substituents independently
      selected from $C_1$-$C_6$ alkyl, halogen, CN, $OR_3$, $NR_3R_4$, or $CONR_3R_4$;
$R_2$ is —$SO_3M$,
$R_3$ and $R_4$ are each independently:
  (a) hydrogen, or
  (b) $C_1$-$C_6$ alkyl optionally substituted with one or more substitutents independently selected from halogen, CN, OH, O($C_1$-$C_6$ alkyl), NH($C_1$-$C_6$ alkyl), N($C_1$-$C_6$ alkyl)$_2$, CONH($C_1$-$C_6$ alkyl), CON($C_1$-$C_6$ alkyl)$_2$, cycloalkyl, heterocycloalkyl, aryl or heteroaryl;
M is hydrogen or a cation;
said process comprising:
  (a) reacting a compound of Formula (Ia) with R1CH2CONHNH2 (Ib), in presence of a coupling agent, to obtain a compound of Formula (Ic);

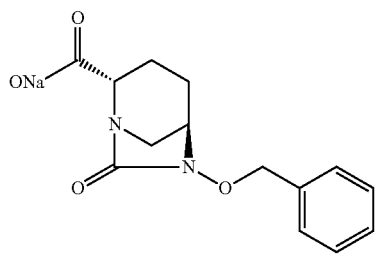

(Ia)

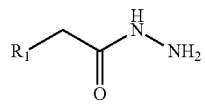

(Ib)

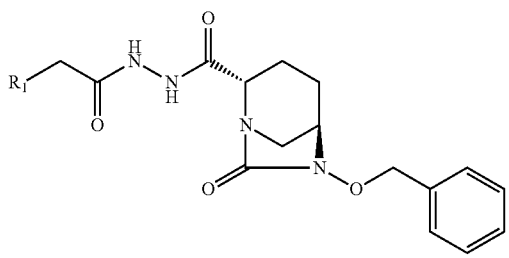

(Ic)

(b) hydrogenolysis of a compound of Formula (Ic) to obtain a compound of Formula (Id);

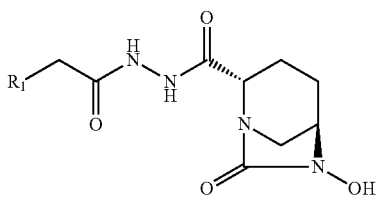

(Id)

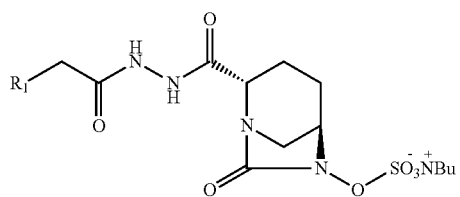

(Ie)

(c) sulfonating a compound of Formula (Id), followed by the treatment with tetrabutyl ammonium sulfate, to obtain a compound of Formula (Ie) and
(d) converting a compound of Formula (Ie) to obtain a compound of Formula (I).

18. The process according to claim 17, wherein the coupling agent in step (a) is selected from 1-ethyl-3-(3-dimethylaminopropyl)carbodiimide hydrochloride, 1-hydroxybenzotriazole, dicyclohexyl carbodiimde or pivalyl chloride.

* * * * *